United States Patent
Allen et al.

(10) Patent No.: US 8,795,192 B2
(45) Date of Patent: *Aug. 5, 2014

(54) SYSTEM AND METHOD FOR CALIBRATING AND DETERMINING HEARING STATUS

(76) Inventors: Jont B. Allen, Mahomet, IL (US); Patricia S. Jeng, Mahomet, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/452,365

(22) Filed: Apr. 20, 2012

(65) Prior Publication Data

US 2012/0265093 A1    Oct. 18, 2012

Related U.S. Application Data

(63) Continuation of application No. 12/046,012, filed on Mar. 11, 2008, now Pat. No. 8,182,431.

(60) Provisional application No. 60/894,432, filed on Mar. 12, 2007.

(51) Int. Cl.
  *A61B 5/12*   (2006.01)

(52) U.S. Cl.
  CPC ..................................... *A61B 5/121* (2013.01)
  USPC .......................................................... 600/559

(58) Field of Classification Search
  USPC .......................................................... 600/559
  See application file for complete search history.

(56) References Cited

U.S. PATENT DOCUMENTS

| | | | | |
|---|---|---|---|---|
| 4,038,496 | A * | 7/1977 | Feezor .............................. | 73/585 |
| 5,792,072 | A * | 8/1998 | Keefe ............................. | 600/559 |
| 5,792,073 | A * | 8/1998 | Keefe ............................. | 600/559 |
| 5,885,225 | A * | 3/1999 | Keefe et al. .................... | 600/559 |
| 6,522,988 | B1 * | 2/2003 | Hou ............................... | 702/122 |
| 6,840,908 | B2 * | 1/2005 | Edwards et al. ............... | 600/559 |
| 7,223,245 | B2 * | 5/2007 | Zoth et al. ...................... | 600/559 |
| 7,496,205 | B2 * | 2/2009 | Kuhnel ............................ | 381/60 |
| 7,715,577 | B2 * | 5/2010 | Allen et al. .................... | 381/312 |
| 7,817,803 | B2 * | 10/2010 | Goldstein ........................ | 381/56 |
| 8,182,431 | B2 * | 5/2012 | Allen et al. .................... | 600/559 |
| 8,241,224 | B2 * | 8/2012 | Keefe ............................. | 600/559 |
| 2003/0083591 | A1 * | 5/2003 | Edwards et al. ............... | 600/559 |
| 2003/0144603 | A1 * | 7/2003 | Zoth et al. ...................... | 600/559 |
| 2005/0013457 | A1 * | 1/2005 | Sheplak et al. ................ | 381/338 |
| 2006/0083395 | A1 * | 4/2006 | Allen et al. .................... | 381/312 |
| 2007/0156063 | A1 * | 7/2007 | Zoth et al. ...................... | 600/559 |
| 2007/0219458 | A1 * | 9/2007 | Jeng ................................ | 600/559 |
| 2008/0194984 | A1 * | 8/2008 | Keefe ............................. | 600/559 |
| 2008/0228101 | A1 * | 9/2008 | Allen et al. .................... | 600/559 |
| 2012/0302859 | A1 * | 11/2012 | Keefe ............................. | 600/383 |

OTHER PUBLICATIONS

Allen et al. "Evaluation of human middle ear function via an acoustic power assessment," Journal of Rehabilitation Research & Development vol. 42, No. 4, Jul./Aug. 2005 pp. 63-78.*

* cited by examiner

*Primary Examiner* — Sean Dougherty
*Assistant Examiner* — Michael C Stout
(74) *Attorney, Agent, or Firm* — Atann Das; Techlaw LLP

(57) ABSTRACT

Method and System for characterizing an incident pressure wave in a hearing test. The method includes introducing a sound signal of a predetermined frequency and amplitude into an ear canal, measuring at least a sound pressure level ($P_m$) in the ear canal, processing information associated with the sound pressure level, obtaining at least an acoustic reflectance (R) based on information associated with the sound pressure level, and determining an incident wave pressure parameter ($P_+$) in the car canal according to the following formula:

$$P_+ = \frac{P_m}{1+R}.$$

9 Claims, 4 Drawing Sheets

SYSTEM AND METHOD FOR CALIBRATING AND DETERMINING HEARING STATUS

CROSS-REFERENCE TO RELATED APPLICATIONS

The present application claims priority under the laws and rules of the United States, including 35 USC §120, to the following patent applications. The present application is a continuation application of, and claims priority to, U.S. application Ser. No. 12/046,012 filed Mar. 11, 2008 which claims priority to U.S. Provisional Application No. 60/894,432 filed Mar. 12, 2007, both of which are incorporated by reference.

BACKGROUND

The present invention relates generally to hearing screening and diagnostic techniques. More specifically, the invention provides a method and system for calibrating hearing equipments and determining hearing status. Merely by way of example, the invention has been applied to audiometer, but it would be recognized that the invention has a much broader range of applicability.

Hearing loss can be categorized by where or what part of the auditory system is damaged. There are three basic types of hearing loss: conductive hearing loss, sensorineural hearing loss and mixed hearing loss.

Conductive hearing loss occurs when sound is not conducted efficiently through the outer ear canal to the eardrum and the tiny bones, or ossicles, of the middle ear. Examples of conditions that may cause a conductive hearing loss include: conditions associated with middle ear pathologies such as fluid in the middle ear from colds, allergies, poor eustachian tube function, perforated eardrum, benign tumors disarticulated ossicles, ossification of ligament, impacted earwax, and infection in the ear canal.

Sensorineural hearing loss occurs when there is damage to the inner ear (cochlea) or to the nerve pathways from the inner ear (retrocochlear) to the brain. Sensorineural hearing loss can be caused by diseases, birth injury, drugs that are toxic to the auditory system, and genetic syndromes. Sensorineural hearing loss may also occur as a result of noise exposure, viruses, head trauma, aging, and tumors.

Mixed hearing loss results when a conductive hearing loss occurs in combination with a sensorineural hearing loss. In other words, there may be damage in the outer or middle ear and in the inner ear (cochlea) or auditory nerve.

Various techniques have been developed for screening hearing problem. For instance, an analysis of the acoustic power reflectance in the ear canal has been shown to be effective in diagnosing conductive hearing loss problems while an otoacoustic emission test (OAE) has been shown to be effective for diagnosing sensorineural hearing loss issues.

Acoustic power reflectance is the measurement of the amount of power being reflected from the ear drum, middle ear structure, and/or cochlea. More specifically, it is defined as the ratio of the forward-moving (incident) pressure wave to the reflected (retrograde) pressure wave. Consider an acoustic pressure wave that travels along an ear canal, as long as no discontinuities exist in the ear canal, the acoustic power that is conveyed by the pressure wave propagates unimpeded to the eardrum. The eardrum then conducts the acoustic power into the middle ear. However, due to mismatch in ear canal impedance, while some of the incident power that reaches the eardrum will enter the middle ear, the remainder is reflected back into the ear canal. The reflected power takes the form of a retrograde pressure wave in the ear canal.

The magnitude and latency of the reflected waves as a function of frequency, is a useful indicator of the status of the middle ear. Reflected acoustic power that is significantly different in magnitude or latency from that of a normal ear will likely reveal the precise nature of a disorder.

The otoacoustic emission test (OAE), on the other hand, measures the sounds that the ear produces in response to stimulation. There are two common types of otoacoustic emissions in clinical use: Transient otoacoustic emissions (TOAEs) or transient evoked otoacoustic emissions (TEOAEs) are sounds emitted in response to a train of acoustic stimuli of very short duration. These stimuli are usually clicks but can be tone-bursts. Distortion product otoacoustic emissions (DPOAEs) are sounds emitted by the cochlear hair cells in response to two simultaneous tones of different frequencies.

While the above mentioned hearing testing techniques are extensively used in the detection of hearing loss, the presence of standing wave can adversely affect calibration of audiometers and also the accuracy of these hearing tests. Therefore, it would be desirable to have hearing test methods and systems that produce result that are affected by reduced distortions from standing waves or even free from any distortion by standing waves.

SUMMARY OF THE INVENTION

The present invention relates generally to hearing screening and diagnostic techniques. More specifically, the invention provides a method and system for calibrating hearing equipments and determining hearing status. Merely by way of example, the invention has been applied to audiometer, but it would be recognized that the invention has a much broader range of applicability.

An embodiment of the present invention provides a method for characterizing an incident pressure wave in a hearing test. The method includes introducing a sound of a predetermined frequency and amplitude into an ear canal, measuring at least a sound pressure level ($P_m$) in the ear canal, processing information associated with the sound pressure level, obtaining at least an acoustic reflectance (R) based on information associated with the sound pressure level, and determining an incident wave pressure parameter ($P_+$) in the ear canal according to the following formula:

$$P_+ = \frac{P_m}{1+R}.$$

Another embodiment of the present invention provides a method for determining a hearing threshold by determining an incident wave pressure parameter and turning it into a power intensity parameter for use in conducting equipment calibrations and hearing loss measurements.

Another embodiment of the present invention provides a method for determining a hearing threshold. The method includes providing a probe suitable for placement in an ear canal, the probe being configured to deliver a tone associated with one or more frequencies and one or more volume levels and further configured to measure one or more sound signals, determining a threshold volume level for the tone, measuring at least a sound pressure level of the ear canal at the threshold volume using the probe; processing information associated with the measured sound pressure level, obtaining an acoustic reflectance based on at least information associated with the measured sound pressure level, determining a threshold value for an incident wave pressure parameter in the ear canal based on at least information associated with the measured sound pressure level and the determined acoustic reflectance, wherein the threshold value for the incident wave pressure parameter representing the hearing threshold.

Another embodiment of the present invention provides a system for determining an incident wave pressure in a hearing test. The system includes a probe adapted to be placed in a ear canal, the probe includes a source transducer for delivering a sound and a receiving transducer for detecting a sound, a signal generator connected to the source transducer, the signal generator being configured to send one or more first electronic signals to the source transducer for delivering the sound, a signal processor connected to the receiving transducer, the signal processor being configured to receive one or more second electronic signals from the receiving transducer and to determine at least a sound pressure level ($P_m$) based on at least information associated with the one or more second electronic signals, a data processor connected to the signal processor, the data processor being configured to receive and process at least information associated with the determined sound pressure level ($P_m$) and to determine an acoustic reflectance (R), and wherein the data processor is further configured to determine an incident wave pressure parameter ($P_+$) in the ear canal according to the following formula:

$$P_+ = \frac{P_m}{1+R}.$$

Another embodiment of the present invention provides a method for characterizing an incident pressure wave in a hearing test. The method includes introducing a sound of a predetermined frequency and amplitude into an ear canal, measuring at least a sound pressure level ($P_m$) in the ear canal, processing information associated with the sound pressure level, obtaining at least an acoustic reflectance (R) based on information associated with the sound pressure level, terminating the ear canal with its own characteristic impedance, and determining an incident wave pressure parameter ($P_+$) in the ear canal according to the following formula:

$$P_+ = \frac{P_m}{1+R}.$$

The present invention has various advantages over conventional techniques. Certain embodiments can provide hearing testing systems and methods that produces results that are affected by reduced influence of standing waves or even free from any influence by standing waves. Some embodiments can provide hearing testing systems and methods that could better distinguish inner ear hearing problems from middle ear hearing problems.

Some embodiments of the present invention can significantly lower the cost of ear screening. For instance, some embodiments of the present invention reduce the number of false-positives in a hearing testing programs by distinguishing middle ear problems from inner ear problems.

Some embodiments of the present invention provide more accurate determination of hearing status by isolating the incident wave pressure measurement from that of measured pressure, thereby eliminating the effects of standing waves. As a result, the power measurement is a better representation of the actual sound power that is being transmitted to the inner ear.

Some embodiments of the present invention provide significant improvement over conventional ear screening methods by taking into account of the retrograde waves. For example, some embodiments of the present invention derive a power measurement that reduces the effect of the retrograde waves on the power measurement, thereby making the measurement more accurate.

In some embodiments of the present invention, the incident wave pressure can be used for better hearing aid fitting.

With a more accurate measurement of the incident power to the ear drum, some embodiments of the present invention allow for a more reliable calibration of the audiometer.

With a more accurate measurement of the sound level delivered to the inner ear, some embodiments of the present invention allow for a more accurate result from the pure tone audiometry, distortion product otoacoustic emission measurements, transient otoacoustic emission measurements, and stimulus frequency otoacoustic emission measurements.

Depending upon embodiment, one or more of these benefits may be achieved. These benefits and various additional objects, features and advantages of the present invention can be fully appreciated with reference to the detailed description and accompanying drawings that follow.

DETAILED DESCRIPTION OF THE INVENTION

Figure 1:
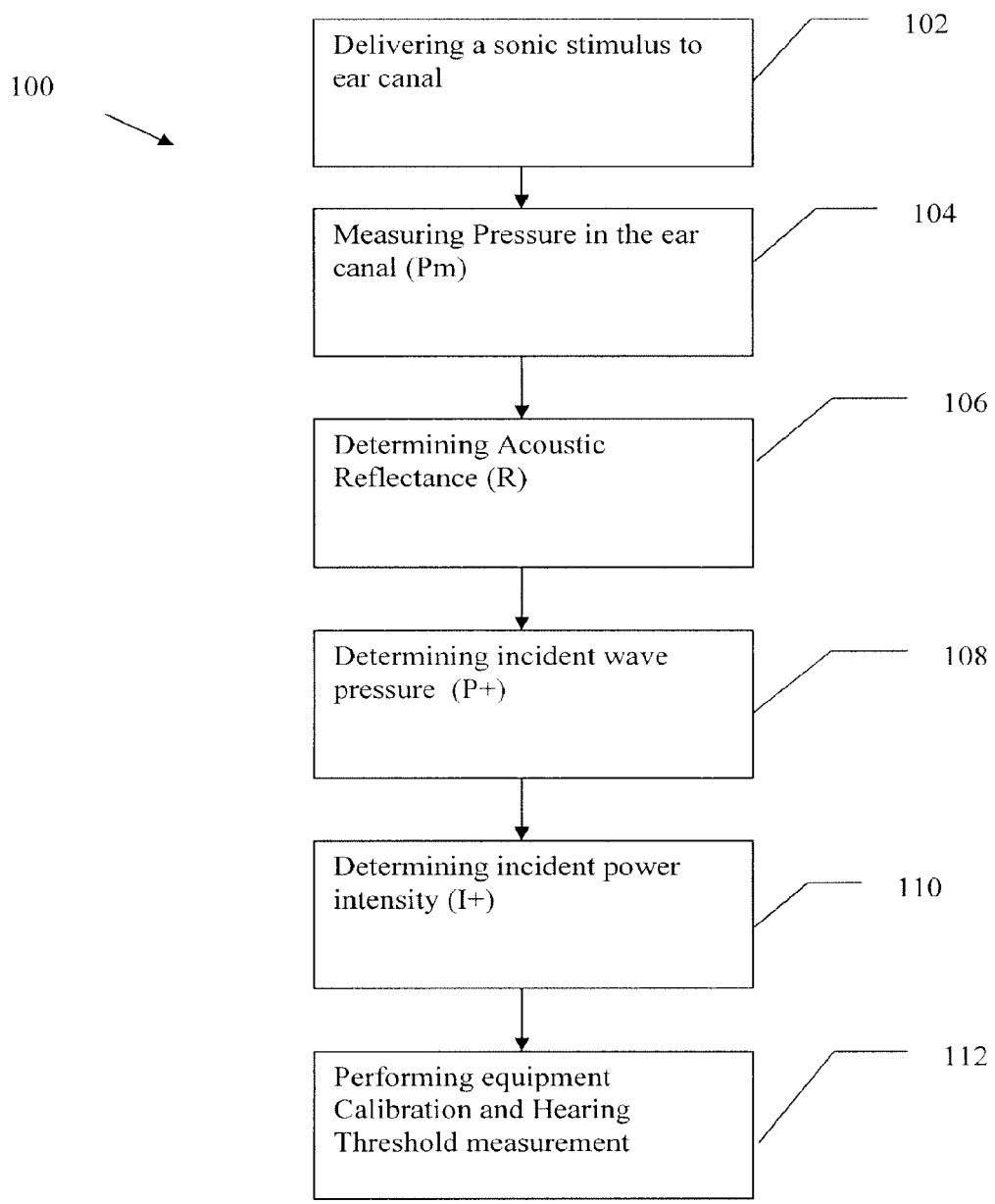
FIG. 1 is a simplified block diagram of a method for determining an incident wave pressure according to an embodiment of the present invention.

The present invention relates generally to hearing screening and diagnostic techniques. More specifically, the invention provides methods and systems for calibrating hearing equipments and determining hearing status. Merely by way of example, the invention has been applied to audiometer, but it would be recognized that the invention has a much broader range of applicability.

As described above, in conventional techniques, the presence of standing waves can adversely affect the results of these hearing tests. Specifically, standing waves are nulls (or nodes) formed from the destructive interaction between the incident and the reflected waves. These pressure nulls are developed at positions where the two waves are out of phase. If the stimulus frequency is such that one of these pressure nulls is near the entrance to the emission probe, then the measured pressure would be substantially attenuated. As a result, there can be a discrepancy as large as 15-20 dB between the sound pressure level measured by the emission probe and the sound pressure level at the eardrum. In other words, because of the pressure cancellation effect of the standing wave, the sound pressure level recorded at the probe may not accurately reflect the actual sound pressure at the eardrum.

The problem is further exacerbated if the patient suffers from mixed hearing loss. In such cases, the conductive hearing loss caused by pathologies in the middle ear will tends to further distort the actual incident power that is delivered to the inner ear. As a result, test result may indicate that a patient suffers inner ear problem even when none exists.

In other words, conventional techniques for calibration and hearing loss detection are often inadequate due to the distortion of the measuring parameters by standing waves and middle ear pathologies. More specifically, conventional calibration techniques, such as Reference Equivalent Sound Pressure Level (RETSPL) defined in the ANSI S3.6 1996 standard or ear canal pressure measurement, fail to compensate for standing wave effect caused by the reflected wave. Recently, there has been some discussion of a real-ear intensity calibration based on a paper entitled "Comparison between intensity and pressure as measures of sound level in the ear canal" published in *J. Acoust. Soc. Am.* 104 in 1998 by Neely S. T. and Gorga, M. P. However, the proposed intensity measurement is solely derived from the overall pressure measurement, which includes power contribution from both the forward and backward wave components. While the use of this total power intensity for calibration and measurement has mitigated some of the distortion problem caused by standing waves, the measurements are still susceptible to a fair amount of standing wave distortion. Therefore, one of the intents of this invention is to propose a new method for calibration and measurement that uses an intensity value derived from the forward component of the measured wave pressure only, thereby avoiding the problems associated with standing wave interference entirely.

FIG. 1 is a simplified block diagram of a method for determining an incident wave pressure according to an embodiment of the present invention. The diagram and the associated description are provided only as an example, which should not unduly limit the scope of the claims herein. One of ordinary skill in the art would recognize many variations, alternatives, and modifications. For instance, while the method described below relates to pure tone audiometry (PTA) only, the described method may easily be adapted for use with various other types of hearing screening methods such as otoacoustic emission (OAE) measurements and auditory brainstem response (ABR) measurements.

The method 100 includes a process 102 for delivering a sonic stimulus to a ear canal, a process 104 for measuring the pressure generated ($P_m$) in a ear canal, a process 106 for providing the power reflectance (R) of the ear canal, a process 108 for determining the incident wave pressure ($P_+$), a process 110 for determining the incident power intensity, and a process for performing equipment calibrations and hearing measurements. Although the above has been shown using a selected sequence of processes, there can be many alternatives, modifications, and variations. For example, some of the processes may be expanded and/or combined. Other processes may be inserted to those noted above. Further detail of the present invention can be found throughout the present specification and more particularly below.

At the process 102, a sonic stimulus is delivered to the ear canal using a sound source transducer positioned at the opening of the ear canal. Depending on the application, the sonic stimulus may be a tone, a chirp, multiple tones, or other stimulus type. In one embodiment, the sonic stimulus can be a pure tone of a predetermined frequency and amplitude. In another embodiment, a pure tone frequency at 1 kHz may be chosen for the hearing test. In yet another embodiment, the tone may be a wide band sweep (chirp) of a range of frequencies within the human audible range. In yet another embodiment, two sound source transducers may be used to generate two pure tones to stimulate a measurable distorted emission from the cochlear hair cells. In yet another embodiment, the sound source transducer is a speaker housed in a ear probe.

At the process 104, the pressure in the ear canal is recorded. In one embodiment, the pressure is measured using a receiving transducer positioned at the opening of the ear canal. In another embodiment, the receiving transducer is a microphone embedded in the same ear probe that houses the speaker.

At the process 106, the power reflectance (R) of the ear canal is computed. In one embodiment, the power reflectance may be derived from the measured pressure as it is disclosed in a paper by Susan E. Voss and Jont B. Allen entitled "Measurement of Acoustic Impedance and Reflectance in the Human Ear Canal." 95 *J. Acoust. Soc. Am.* 372 (January 1994). In another embodiment, the acoustic reflectance may be measured using one of a plurality of reflectance measurement systems, such as the MEPA3 Clinical Reflectance System, manufactured by Mimosa Acoustics, Inc.

At the process 108, the incident wave pressure ($P_+$) in the ear canal is extracted from the measured pressure ($P_m$). In one embodiment, the incident wave pressure ($P_+$) is a function of the measured ear canal pressure ($P_m$) and the ear canal reflectance (R) according to the following equation:

$$P_+(f) = \frac{P_m(x, f)}{1 + R(x, f)}$$

where x is the distance of the microphone from the ear canal and f is the frequency of the selected sonic stimulus.

As shown in the equation above, while the measured pressure ($P_m$) and the reflectance (R) are both functions of x and f, the ratio of $P_m$ to R is a function of the f only. As a result, the incident wave power intensity is independent of the probe location and thus free from any distortion by standing waves.

At the process 110, once the incident wave pressure is computed, the incident power intensity ($I_+$), which is defined as power per unit area, may be derived from the following equation:

$$I_+ = \frac{|P_+|^2}{Z_0},$$

where $Z_0$ is the wave characteristic impedance that is defined by the following equation:

$$Z_0(x, s) = \frac{\rho_0 c}{A(x)},$$

where $\rho_0$ is the density of air, c is the speed of sound, and A(x) is the area of the ear canal.

Therefore, the incident power intensity ($I_+$) may be calculated from the measured pressure ($P_m$) according to the following equation:

$$I_+ = \frac{|P_m^2|}{Z_0(|1 + R|)^2}.$$

In one embodiment of the present invention, the ear canal is terminated in the characteristic impedance of the ear canal ($Z_0$) to prevent the retrograde pressure (P−) from affecting incident wave intensity value.

At the process 112, the calculated $P_+$ or $I_+$ is used for performing calibration of the audiometer or making hearing measurements. For example, a key concept behind certain embodiments of the present invention is that P+ is more highly correlated to the hearing threshold than the microphone pressure Pm, because the function 1+R(f) removes the effect of standing waves. For another example, the calculated $P_+$ or $I_+$ may be used for real-ear calibration of the audiometer. Because the calculated $P_+$ and $I_+$ are free from the influence of standing waves and middle ear pathologies, and because they are independent of the position of the probe in the ear canal (they do not depend on x), they provide a more accurate calibration for the audiometers. The calculated $P_+$ and $I_+$ may also be used in a various OAE measurements such as distortion product otoacoustic emission measurement, transient otoacoustic emission measurement, and stimulus frequency otoacoustic emission measurement.

Although the above has been shown using a selected sequence of processes, there can be many alternatives, modifications, and variations. For example, some of the processes, such as the processes 102, 104, and 106, may be combined. In another example, a process, such as the process 110, may be skipped.

In another embodiment, we know that the energy travels at the wave speed in the forward direction, is reflected by inhomogeneities and by spreading of the wave as it propagates, and then travels in the reverse direction. The product of the wave pressure (P) and wave velocity (U) determines the wave intensity. (Here, the wave velocity is a distinctively different entity from speed of sound. In the following discussion, we shall use the term "velocity" or "U" to mean the acoustic velocity of the wave and the term "speed" or c to indicate the velocity of the wave front. As shown above, the wave impedance is given by $$Z_0 = \frac{\rho_0 c}{A},$$

where c is the speed of sound. On the other hand, the wave power is given by P*U where P is the pressure and U is the wave velocity.) In the general case the wave speed (c) can depend on frequency and position. We explore the relationships between the forward and backward traveling wave variables (pressure and volume velocity) $[P_+(x,\omega), U_+(x,\omega)]$ and $[P_-(x, \omega), U_-(x, \omega)]$ for inhomogeneous media, and then give formulas for the forward and backward intensity flow, and its velocity, in terms of the medium's constitutive relations.

Figure 2:
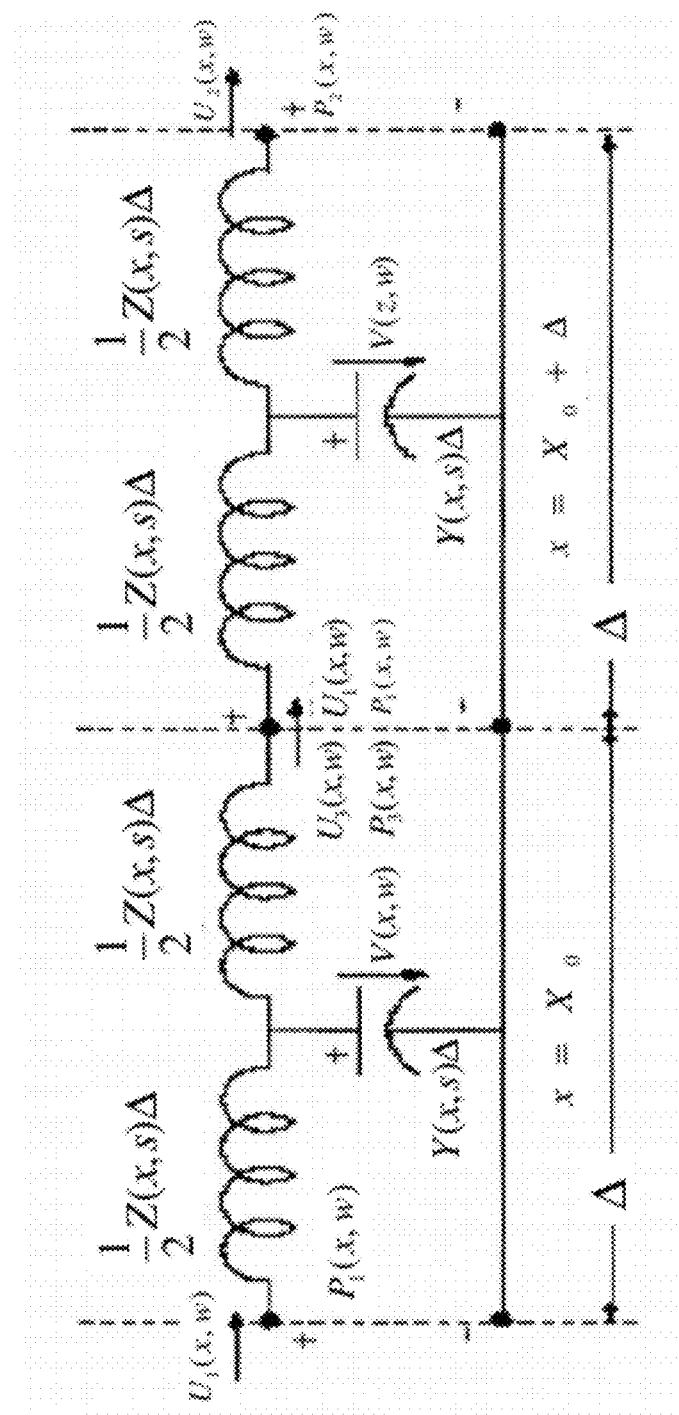
FIG. 2 shows two conventional sections of the basic transmission line model according to an embodiment of the present invention.

FIG. 2 shows two conventional sections of the basic transmission line model, as a lumped parameter electrical circuit. Inductance represents mass per unit length and while the capacitance represents stiffness per unit length, in such a representation for a section Δ meters long. In the following discussion, we shall denote $p_\pm(x, t)$ as the wave pressure in the forward (anterograde) and reverse (retrograde) directions, and $u_\pm(x, t)$ as the anterograde and retrograde wave velocities. In some cases we shall let u represent the volume velocity. The Fourier and Laplace transforms are indicated by upper case letters. For example $p_+(x, t) \leftrightarrow P_+(x, \omega)$. When subscripts are required, the ± will be indicated as superscripts (e.g., $P_i^+(x, \omega)$). The symbol $\leftrightarrow$ indicates a transform pair.

A medium's wave properties are characterized by the per-unit length series impedance $\mathcal{Z}(x, s)$ and the per-unit length shunt admittance Y (x, s), denoted here as constitutive relations. In the ear canal the medium is air and $\mathcal{Z}$ is determined by the density of the air and Y by the air's stiffness.

Intensity has direction, collinear with that of the velocity. The total pressure and particle velocity have corresponding forward and retrograde components. It follows from wave linearity, that without loss of generality, the pressure (a force per unit area) may be written as a sum of anterograde $P^+$ and retrograde $P^-$ propagated pressure waves as, for example, $$P(x,\omega) = P^+(x,\omega) + P^-(x,\omega). \tag{1}$$

Likewise, the axial velocity U (a flow) may be expressed as, for example, a "sum" of anterograde and retrograde axial velocity traveling wave components $$U(x,\omega) = U^+(x,\omega) - U^-(x,\omega). \tag{2}$$

The retrograde velocity component is negative because velocity, like intensity, has direction, whereas pressure is a scalar, without direction.

The ratio of the pressure and velocity for forward and backward traveling waves is equal to an inhomogeneous impedance we call the characteristic impedance, denoted $\zeta_0(x, t)$ in the time domain and $Z_0(x, s)$ in the frequency domain, such that $$\zeta_0(x, t) \leftrightarrow Z_0(x, s) = \frac{P_\pm(x, \omega)}{U_\pm(x, \omega)}, \tag{3}$$

independent of the direction of the wave (as above). For homogeneous waves Eq. 3 is well known.

The two inhomogeneous material properties $\mathcal{Z}(x, s)$ and Y (x, s) define the wave properties via two functions, the wave characteristic impedance, for example, can be defined as $$Z_0(x, s) \equiv \sqrt{\frac{\mathcal{Z}(x, s)}{\mathcal{Y}(x, s)}}, \tag{4}$$

and the wave propagation function $$\gamma(x,s) = \sqrt{\mathcal{Z}(x,s)\mathcal{Y}(x,s)}. \tag{5}$$

The wave characteristic impedance is important because it is used in the definition of wave intensity, while the wave propagation function determines the speed of sound (c), as a function of position and frequency.

Given Eq. 3 it follows that the average forward (+) and retrograde (−) intensity is, for example, $$\bar{I}_\pm(x,\omega) = \tfrac{1}{2}\mathfrak{R}\, P_\pm U_\pm^* = \tfrac{1}{2}\mathfrak{R}\, Z_0 |U_\pm(x,\omega)|^2 = \tfrac{1}{2}\mathfrak{R}\, Y_0(x,s) |P_\pm(x,\omega)|^2, \tag{6}$$

where $Y_0 = 1/Z_0$ and $\mathfrak{R}$ indicates the real part.

The pressure and velocity are related by the line impedance Z(x, s), defined as the pressure over the velocity $$\zeta(x, t) \leftrightarrow Z(x, s) \equiv \frac{P(x, \omega)}{U(x, \omega)} = \frac{P^+ + P^-}{U^+ - U^-} = Z_0(x, s)\frac{1 + \mathcal{R}(x, s)}{1 - \mathcal{R}(x, s)}. \tag{7}$$

where we have used our previous definitions Eq. 1, Eq. 2 and Eq. 3. In the time domain $p(x, t) = \zeta(x, t) * u(x, t)$ at every point x on the line. In Eq. 7 the reflectance R(x, s) is defined in the frequency domain as the transfer function between incident and reflected waves at a location x along the line, namely $$R(x, s) \equiv \frac{P_-(x, \omega)}{P_+(x, \omega)} = \frac{U_-(x, \omega)}{U_+(x, \omega)}. \quad (8)$$

The wave variables $P\pm$, $U\pm$ are related to each other via the reflectance. From the above definition of the reflectance, and from Eq. 7, a little algebra gives, as an example, $$R(x, s) = \frac{Z(x, s) - Z_0(x, s)}{Z(x, s) + Z_0(x, s)}. \quad (9)$$

For example, in the time domain $p_-(x, t) = q(x, t) * p_+(x, t)$, where * represents the time convolution operator, namely $$p_-(x, t) = \int_{\tau=0}^{\infty} -q(x, \tau) p_+(x, t-\tau) d\tau.$$

A similar relation holds the velocity wave variables. Given $Z(x, s)$ and $Z_0(x, s)$, one may find the reflectance $R(x, s)$ from Eq. 9. Alternatively, given $R(x, s)$ one may find the normalized impedance $Z(x, s)/Z_0(x,s)$. Physically this means that the reflectance is mathematically related to the impedance, normalized by $Z_0$. Thus the definition of the characteristic impedance for inhomogeneous and dispersive media plays a fundamental role in relating wave variables to intensity flow.

The wave equation for the pressure $p(x, t)$ is, as an example, $$\frac{\partial^2 p(x, t)}{\partial x^2} = \frac{1}{c^2} \frac{\partial^2 p(x, t)}{\partial t^2}. \quad (10)$$

The general solution of the wave equation is, for example, $$p(x,t) = p_+(t-x/c) + p_-(t+x/c), \quad (11)$$

where $p_+(\xi)$ and $p_-(\xi)$ are two arbitrary functions. This solution tells us that the wave equation supports forward and backward propagated "waves," which are represented in two arbitrary functions $p_+$ and $p_-$, traveling at the speed of sound c (or if one considers the electromagnetic case, of light), in the forward and backward directions. These two solutions ($p_+$ and $p_-$) are denoted as wave variables, since they are of the form of forward and backward traveling pressure (voltage) or velocity (current) waves. Equation 11 indicates that any function, having arguments $t\pm x/c$, is a solution of the wave equation. The incident wave is denoted the anterograde wave, while reverse (reflected) traveling wave is denoted the retrograde wave.

The units of the waves are indeterminate and open to choice. For acoustic problems the waves may be pressure p or velocity u. In electrical problems it may be voltage, current, electric or magnetic field, scalar or vector, or even probability waves, as in quantum mechanics. Note, for example, that by simple linear transformation, the solution of a linear, time-invariant (i.e., LTI), dispersionless (c is independent of frequency f) second-order differential equation (Eq. 10), may be written either in terms of (1) the sum of two pressure waves $[p_+(x, \omega), p_-(x, \omega)]$ (for the acoustic case), or (2) two velocity waves $[u_+(x, \omega), u_-(x, \omega)]$, or a combination of (3) pressure and velocity $[p(x, \omega), u(x, \omega)]$. In each case appropriate boundary conditions are required to provide the scaling of the two degrees of freedom provided by these various representations.

The wave variables in equation 11 are very physical as they describe the solution of the wave equation in a natural manner, as waves going in the two directions. There is something special about each of these waves in that they transport energy in the two directions, in an uncoupled manner. The waves are uniquely specified in terms of the intensity property. The pressure is the sum of the forward and reverse pressure, and each wave pressure (or velocity) uniquely defines the intensity via the characteristic impedance. Since the two intensity are independent (they depend only on the boundary conditions), the wave variables are uniquely specified for this case.

With reference to FIG. 2, the basic equation for dispersive inhomogeneous media: an important and well known generalization of Eq. 10 is the LTI, causal, dispersive, inhomogeneous pair of first order equations $$\frac{d}{dx}\begin{bmatrix} P(x, \omega) \\ U(x, \omega) \end{bmatrix} = -\begin{bmatrix} 0 & \mathcal{Z}(x, s) \\ \mathcal{Y}(x, s) & 0 \end{bmatrix}\begin{bmatrix} P(x, \omega) \\ U(x, \omega) \end{bmatrix}. \quad (12)$$

where $P(x, \omega)$ is the pressure (or voltage), $U(x, \omega)$ is the velocity (or current), $$Z(x,s) = R(x,s) + sL(x,s), \quad (13)$$

is the per unit length series impedance, and $$y(x,s) = G(x,s) + sC(x,s) \quad (14)$$

is the per unit length shunt admittance, where by definition R and G are the real part of $\mathcal{Z}$ and Y, and in a loss-less medium are zero.

One cannot determine the formula for the wave speed c in terms of $\mathcal{Z}$ and Y from Eq. 10 without an additional relationship. However given Eq. 12, this relation may easily be determined, since $\mathcal{Z}$ and Y are explicitly specified in the formulation. Equation 12 is called the Webster Horn equation, (in acoustic applications), or the Telegraph equation (in electromagnetic applications). It follows that Eq. 12 is more general that Eq. 10, and represents a generalization in the sense that it defines the waves directly in terms of the medium's constitutive relations $\mathcal{Z}(x, s)$ and $Y(x, s)$, in general can be location and frequency dependent. Equation 12 it is typically written as a single second-order equation.

The constitutive relations $\mathcal{Z}(x, s)$ and $Y(x, s)$ may be determined only by an experiment on a given physical system, or by a theoretical model. They define a wave medium's material properties.

For lossless homogeneous cases (L and C constant and $R(x, s) = G(x,s) = 0$), Eq. 12 trivially reduces to the wave equation Eq. 10 having solution Eq. 11 and the propagation function indirectly specifies the wave speed as Eq. 5, which says that for Eq. 10, $c = 1\sqrt{LC}$. Equally important, the wave's characteristic impedance is given by Eq. 4. These relations are important because they connect the wave properties $\gamma$ and $Z_0$ to the physical constitutive relations. As an example, for acoustic wave propagation, $L = \rho_0$, $C = \gamma_0 P_0$. The speed of sound in air is therefore $c = \sqrt{\gamma_0 P_0/\rho_0}$, which is 331 [m/s], assuming $\rho_0 = 1.23$ [kgm/m$_3$], $\gamma_0 = c_p/c_v = 1.4$ and $P_0 = 105$ [Pa]. Furthermore $P\pm/U\pm = Z_0 = \rho_0 c = 407$ [MKS-Rayls].

From Eq. 9, both the characteristic impedance $Z_o$ and a load impedance Z are required when calculating the reflectance. This problem may be solved by replacing the inhomogeneous transmission line by its Thevenin characteristic impedance, loaded by $Z_L(s)$. In this view, the characteristic impedance is defined as the Thevenin source impedance looking into a very short (infinitesimal) piece of the line. When we impulse this system, and restrict time to very short times less than δ, (say of a few microseconds), only the waves in the region δx=cδ$_t$ can play a role in the determination of g(δ$_t$), due to the limited time and limited speed of sound.

For the case in hand, where $Z_0(x)$ does not depend on frequency, then its inverse Fourier transform is, for example, $$\zeta(x,t)=z_0(x)\delta(t) \longleftrightarrow Z_0(x) \quad (15)$$

We call $Z_0(x)$ the surge impedance. It follows from Eq. 7 that in this case R(x, s)=0. We summarize this property by saying that the characteristic impedance is strictly local.

Power and wave variables: In the homogeneous case the forward and backward wave solutions of Eq. 12 are independent, and obey Ohm's Law Eq. 3.

Working in the time domain, the instantaneous intensity I (x, t), at every location x and time t, may be expressed in terms of wave variables $$I(x,t) \equiv p(x,t)u(x,t)=[p^+(x,t)+p^-(x,t)][u^+(x,t)-u^-(x,t)], \quad (16)$$

where u is the particle velocity. Expanding this gives the total intensity (at every time instant t and every location x) in terms of these wave variables $$I(x,t)=p^+(x,t)u^+(x,t)-p^-(x,t)u^-(x,t)+[p^-(x,t)u^+(x,t)-p^+(x,t)u^-(x,t)]. \quad (17)$$

The first term on the right is denoted the forward traveling (anterograde) intensity $$I^+(x,t) \equiv p^+(x,t)u^+(x,t), \quad (18)$$

while the second $$I^-(x,t) \equiv p^-(x,t)u^-(x,t) \quad (19)$$

is denoted the reflected (retrograde) intensity. This leaves the third term in square brackets, which we denote the cross-intensity $$I_c(x,t) \equiv [p^-(x,t)u^+(x,t)-p^+(x,t)u^-(x,t)]. \quad (20)$$

Lossless homogeneous case: Eq. 3 requires that the cross-intensity is zero, because $$Z_0 \equiv \sqrt{\frac{L}{C}} = \frac{P^+}{U^+} = \frac{P^-}{U^-} \quad (21)$$

is a constant. Transforming Eq. 21 to the time domain results in $p_\pm = Z_0 u_\pm$. Substitution into the cross-intensity and factoring out the common constant $Z_0$ results in $$I_c(x,t)=Z_0(x)[u^-(x,t)u^+(x,t)-u^+(x,t)u^-(x,t)]=0. \quad (22)$$

In conclusion, for the lossless homogeneous system $$I(x,t)=I^+(x,t)-I^-(x,t), \quad (23)$$

namely the intensity absorbed is the forward traveling intensity less the backward traveling intensity. This physically makes sense in the sense that the intensity either is traveling one way or the other (homogeneous property), since no energy is burned up in the network (lossless property). The cross-intensity is always zero since there is no fixed relationship between waves going in the two directions.

In the case of a lossless inhomogeneous, when L(x) and C(x) are independent of frequency, then both the reflection coefficient R(x) and $Z_0$ do not depend on frequency. As for the lossless inhomogeneous case, cross-intensity must be zero since then using Eq. 9 given $_\varrho(t)=R(x)\delta(t)$, leading to, for example, $$I_c(x,t)=R(x)[p_+(x,t)u_+(x,t)-p_+(x,t)u_+(x,t)]=0. \quad (24)$$

Thus for the lossless inhomogeneous case, Eq. 23 will hold, since R(x) is a real and independent of frequency.

In the general case, when the constitutive relations depend on frequency (dispersive case), the cross-intensity is not zero, as there must be locally stored energy in the reactive terms. We deal with this case in the frequency domain with the following proofs.

The following is a second proof, which demonstrates Eq. 23 directly. From the basic definitions $$I(s,x)=\tfrac{1}{2}\Re\,[PU^*]=\tfrac{1}{2}\Re\,[(P_++P_-)y_0(P_+-P_-)^*] \quad (25)$$

resulting in Eq. 23

$$\tfrac{1}{2}\Re\, Y|P|^2=\tfrac{1}{2}Y_0|P_+|^2-\tfrac{1}{2}Y_0|P_-|^2, \quad (26)$$

where Y is the ratio of the total volume velocity U divided by the total pressure $P_m$.

This follows because the cross term is purely imaginary, namely $$P_+^*P_--P_+P_-^*=2j\Im P_+\Im P_-, \quad (27)$$

thus after taking the real part we get zero.

This may be the most intuitive proof: We wish to show Eq. 23 is true, in the frequency domain:

$$I(s) \equiv \frac{1}{2}\Re\, PU^* = \frac{|P|^2}{2}\Re\, Y \quad (28)$$

Since $P=P_++P_-=P_+(1+R)$ and using $$I_+ = |P_+|^2\frac{Y_0}{2},\; I(s) = \frac{Y_0}{2}|(1+R)P_+|^2\Re\left(\frac{Y}{Y_0}\right) \quad (29)$$

We need the real part of $Y/Y_0$ which is given by, for example, $$\Re\,\frac{Y}{Y_0} = \Re\,\frac{1-R}{1+R} = \frac{\Re\,(1-R)(1+R^*)}{|1+R|^2} = \frac{1-|R|^2}{|1+R|^2} \quad (30)$$

Using this result in our expression for the total intensity gives equation 23 as desired.

The propagation of these waves is determined by a locally defined propagation function Eq. 5, that also depends exclusively on the constitutive relations. It immediately follows that intensity waves are defined for each of these waves (Eq. 6).

For the case of homogeneous wave propagation, the waves are exclusively coupled at the boundaries. In the inhomogeneous case, reflections occur everywhere the impedance changes (e.g., where $\epsilon(x,s)\neq 0$).

The exponential horn is a helpful example, since the exact closed form solution is known. It has been shown that an approximation of the input impedance looking into an exponential horn can be a parallel combination of a mass and resistive terms. The characteristic impedance $Z_0(x, s)$ is distinct from $Z_r(x, s)$ or $Z_l(x, s)$, which are the input impedances looking right and left from point x into an infinite piece of horn respectively. Since the characteristic impedance is local, it is not depended on direction. These are key properties of the characteristic impedance which are used in the definition of the independent wave intensities (Eq. 6), coupled only by reflections due to inhomogeneities in the medium. It would be interesting to know how these definitions generalize to cases of losses and dispersive constitutive relations.

Properties of $q(x, t) \leftrightarrow R(x, s)$: The reflectance is q(x, t) zero for t=0+ if and only if the impedance is continuous in space, Namely R(x,t) is strictly causal only when $Z_0(x^-)=Z_0(x^+)$, such that the impedance $Z_0(x, s)$ has no jumps. When there is a jump, then the real part of $R(s,x) \equiv (Z-Z_0)/(Z+Z_0)$ will not be zero. This can be easily seen by writing down the expression for r(t) as the inverse Laplace transform of R(s,x), and then setting t–0 in the expression. The imagine part of R is zero, due to the real property of r(t), and the real part of R(s,x) gives r(t=0,x), and is zero. The real part of a complex characteristic impedance $\Re Z_0$ is known as the surge impedance. It is zero if $\Re Z = \Re Z_0$ are equal, namely if the surge impedance of Z and $Z_0$ are equal. This requires continuity of $Z_0(x,s)$ at x. In general, when the load impedance $Z_0(x, s)$ has the surge impedance $Z_0(x, s)$, the reflectance is strictly causal. For example, this is easily seen by writing the expression for the Laplace transform of g(x,t) evaluated at t=0, The imaginary part of the integrand is then zero, due to the real property (i.e., $R^*(-\omega)=R(\omega)$), where * is the symbol for conjugate, while the real part evaluates to g(x,0), which is zero when the surge impedance is $Z_0$.

The wave coupling is summarized most dramatically in terms of the wave reflectance, Eq. 9, since this goes to zero when $\epsilon(x, s)=0$. In the time domain reflectance may be expressed as a convolution $p_\pm(x,t)=q(x, t)*p_\pm(x, t)$, where * indicates convolution with respect to time and $q(x,t) \leftrightarrow R(x,s)$ represent a Laplace transform pair. When R(x) is independent of frequency, $q(x,t)=R(x)\delta(t)$.

Because the incident pressure ($P_+$) and intensity ($I_+$) is not a function of x, the distance placement of the receiving transducer, it's value is not affected by the distorting effect of standing waves. Further, assuming that the power absorbed by the middle ear is negligible, the incident power intensity ($I_+$) is a good measurement of how much power has been actually delivered to the inner ear. As a result, any hearing loss measurement using the incident power intensity would be much more reliable.

Armed with measurements of the power reflectance (R) and the incident wave pressure ($P_+$), one may quickly determine the hearing status of a patient. In one embodiment, The magnitude of the power reflectance value |R|, which is between 0 and 1, measured at a pure tone may be used to detect problems with the middle ear while the value of the incident wave pressure ($P_+$) at the same frequency may be used to detect inner ear problems. For instance, if |R| is approaching a low level of between 0.1 and 0.3, it is a clear indication that the middle ear is fine because most of the sound has been absorbed through the middle ear. On the other hand, if |R| is approaching a high level of between 0.8 and 0.95, it is a clear indication that there are middle ear problems because most of the sound energy is reflected back.

Take, as an extreme example, the case when |R| is approaching 0, it indicates that close to 100% of the sound energy has been transmitted into the middle ear. In that case, one can safely assume that the patient does not have any middle ear pathologies. On the other hand, if |R| is approaching 1, it indicates that close to all of the sound has been reflected away from the middle ear. As a result, one may safely conclude that the patient has problems with its middle ear.

Similarly, according to another embodiment, since the value of $P_+$ is a close approximation of the sound energy that reaches the inner ear, it is a reliable indicator of inner ear problem. For instance, if the measured threshold $P_+$ for a patient is much more than 20 dB-SPL for a 1 k Hz pure tone, then it is a clear indication that the patient suffers from inner ear problem.

In some embodiment, the $P_+$ value may be used for hearing aid fitting, reducing the variability in measurements and improving the efficiency of the hearing aid.

Figure 3:
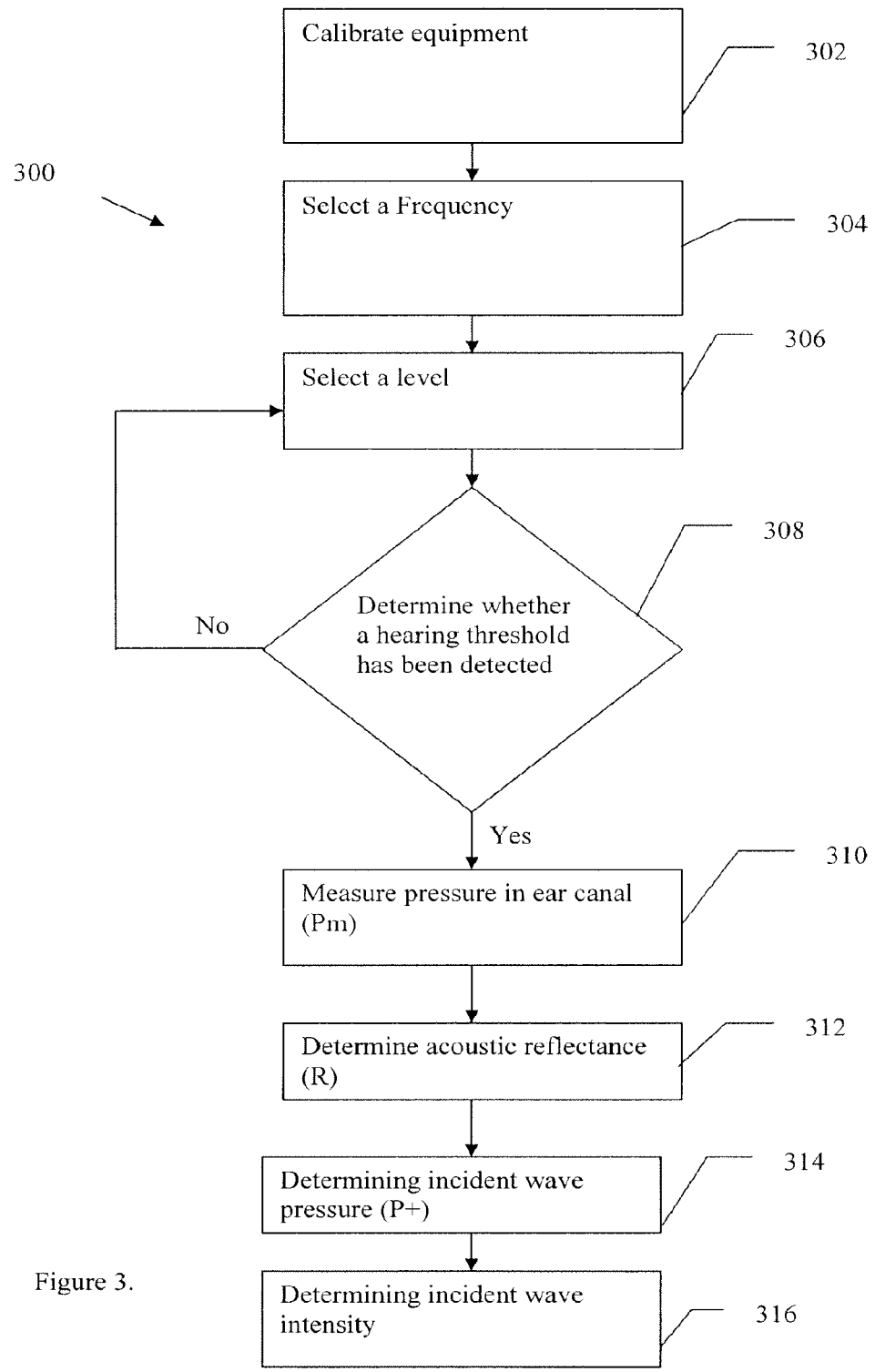
FIG. 3 is a simplified block diagram of a method for determining a hearing threshold according to an embodiment of the present invention.

FIG. 3 is a simplified block diagram of a method for determining a hearing threshold according to an embodiment of the present invention. Merely as an example, the method depicted relates to a pure tone audiometry (PTA) hearing test. However, the described method may easily be adapted for use with various other types of hearing loss tests such as OAE measurements and auditory brainstem response (ABR) measurements.

The method 300 includes a process 302 for calibrating an audiometer, a process 304 for selecting and generating a test tone frequency, a process 306 for selecting and generating a sound source volume level, a process 308 for determining whether a hearing threshold has been detected, a process 310 for measuring the threshold pressure ($P_m$), a process 312 for determining the reflectance (R), and a process 314 for determining the incident wave pressure ($P_+$) and a process 316 for determining a hearing status.

At the process 302, the audiometer is being calibrated. For example, the main objective of calibration is to make sure that the audiometer is making consistent measurements thereby allowing abnormal results to be distinguished from those of typical normal ears. In one embodiment, the audiometer may be calibrated with the traditional RETSPL method. In another embodiment, calibration may be carried out using an impedance cavity as it is shown and described in U.S. Patent Application No. 2007/0219458 entitled "Method and System for Determining Hearing Status." In yet another embodiment of the present invention, calibration may be carried out in a real-ear situation using the incident pressure ($P_+$), the incident power intensity parameter ($I_+$), or absorbed intensity value that is determined by the process described below.

At the process 304, a test tone frequency is selected. Depending on the application, the frequency may be selected from a wide range of frequencies that is audible to a normal human ear, which typically ranges from 100 Hz to 20 k Hz.

At the process 306, a sound source volume level is selected and delivered to the ear canal. At the process 308, a determination is made of whether a hearing threshold has been detected. The two processes 306 and 308 may be repeated until a hearing threshold has been detected as described herein:

In one embodiment, the sound source volume level is turned down in decremental steps from a volume level that a subject can hear, like 70 dB. Then, the level is turned down in large steps (for example, 20 dB) until it cannot be heard. Then the process is repeated again, starting at the last audible level, but in a smaller steps. This is repeated until the threshold is determined to within 5 dB.

At the process 310, the pressure ($P_m$) in the ear canal is measured. In one embodiment, the pressure is measured using a microphone positioned at the opening end of the ear canal.

At the process 312, the power reflectance (R) of the tested ear is determined. In one embodiment, the power reflectance may be derived from the measured pressure as it is disclosed in a paper by Susan E. Voss and Jont B. Allen entitled "Measurement of Acoustic Impedance and Reflectance in the Human Ear Canal." 95 *J. Acoust. Soc. Am.* 372 (January 1994). In another embodiment, the acoustic reflectance may be measured using one of a plurality of reflectance measurement systems such as the RMS/MEPA3 manufactured by Mimosa Acoustics, Inc.

At the process 314, the pressure measurement in the ear canal is converted into incident wave pressure ($P_+$). In one embodiment, the incident wave pressure ($P_+$) is also called the forward wave pressure. In another embodiment, the incident wave pressure ($P_+$) is derived from the ear canal pressure measurement ($P_m$) and the ear canal reflectance (R) using the following equation:

$$P_+(f) = \frac{P_m(x, f)}{1 + R(x, f)}$$

While the embodiment shown in FIG. 3 is adapted for use in pure tone audiometry, the method can be easily adapted for use with various OAE measurements such as distortion product otoacoustic emission measurements, transient otoacoustic emission measurements, and stimulus frequency otoacoustic emission measurements.

Moreover, according to certain embodiments, at the process 316, a hearing status is determined. For example, such determination is performed based on at least the power reflectance (R) and the incident wave pressure ($P_+$). In one embodiment, the power reflectance value (R) measured at a pure tone frequency of 1 kHz may be used to detect problems with the middle ear while the result from using incident wave pressure ($P_+$) at the same frequency may be used to detect inner ear problem.

For example, if R is approaching a low level (e.g., 0 for 1 kHz pure tone), the middle ear is considered normal, but if R is approaching a high level (e.g., 1 for 1 kHz pure tone), the middle ear is considered abnormal. In another example, if the measured threshold $P_+$ for a patient is much more than a threshold level (e.g., 20 dBspl for 1 kHz pure tone), the inner ear is considered abnormal.

As discussed above and further emphasized here, FIG. 3 is provided only as an example, which should not unduly limit the scope of the claims herein. One of ordinary skill in the art would recognize many variations, alternatives, and modifications. For example, in some embodiments, the process 316 can be skipped. In another example, the process 314 is performed to determine the incident wave pressure, but the incident power intensity is not determined at the process 314.

Figure 4:
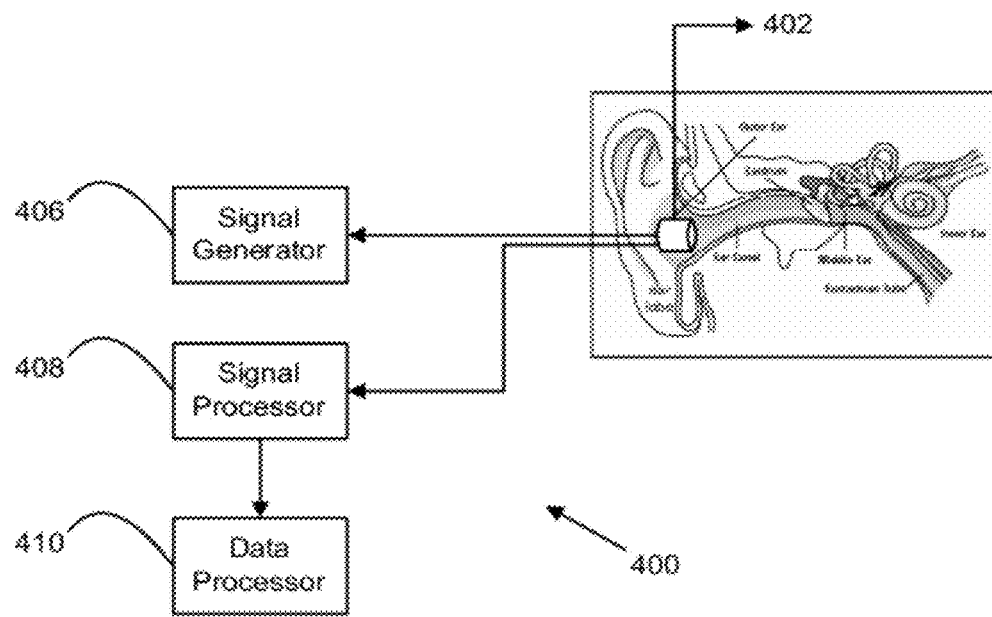
FIG. 4 is a simplified diagram illustrating a system for determining an incident wave pressure according to an embodiment of the present invention.

FIG. 4 is a simplified diagram illustrating a system 400 for determining an incident wave pressure according to an embodiment of the present invention. The system 400 includes a probe 402, a signal generator 406, a signal processor 408, and a data processor 410. According to certain embodiments, the system 400 can be used for screening and/or diagnosing hearing disorders.

As shown in FIG. 4, the probe 402 is connected to the signal generator 406 and the signal processor 408, and the signal processor 408 is connected to the data processor 410. According to an embodiment, the system 400 includes a probe 402 being adapted to be placed inside a ear canal 404. The probe 402 may include a source transducer for making a sound and a receiving transducer for detecting sounds. The source transducer in the probe 402 is connected to a signal generator 406 while the receiving transducer 402 is connected to a signal processor 408. The signal generator 406 is responsible for delivering a signal to the source transducer for the production of one tone, multiple tones, or a sweep of continuous tones. The signal processor 406 receives signals from the receiving transducer in the probe 402 and turns them into pressure measurements ($P_m$). A data processor 410 is connected to the signal processor 408. The data processor 410 receives the pressure measurements ($P_m$) from the signal processor 408 and computes the value of a corresponding power reflectance (R). With $P_m$ and R, the data processor 410 further computes the incident wave pressure ($P_+$) according to the formula shown above.

According to some embodiments, the data processor 410 then computes the incident wave intensity ($I_+$) according to the following equation:

$$I_+ = \frac{Y * |P_m^2|}{(|1 + R|)^2}$$

In the embodiment of the present invention described above, the sound could be a pure tone signal that is customarily used for hearing diagnosis. For instance, the sound could be pure tone at 1 kHz, a frequency that is commonly use for detecting middle ear pathologies. In other embodiments, the sound could be multiple tones, a continuous sweep (chirp) of frequencies in the audible range, or other stimulus types. Such sounds would be ideal for performing other hearing test such as otoacoustic emission measurements and the characterization of the frequency response of a ear canal. In yet another embodiment, the signal generator 406, the signal processor 408, and the data processor 410 may be performed by a computer device configured to generate signals, receive signals, process signals, and calculate for a desirable result.

The present invention has various advantages over conventional techniques. Certain embodiments can provide hearing testing systems and methods that produces results that are affected by reduced influence from standing waves or even free from any distortion by standing waves. Some embodiments can provide hearing testing systems and methods that could better distinguish inner ear hearing problems from middle ear hearing problems.

Some embodiments of the present invention can significantly lower the cost of ear screening. For instance, some embodiments of the present invention reduce the number of false-positives in a hearing testing programs by isolating middle ear problems from inner ear problems.

Some embodiments of the present invention provide more accurate determination of hearing status by isolating the incident wave pressure from that of measured pressure, the present invention eliminates the effects of standing waves. As a result, the computed incident pressure is a better representation of the actual sound pressure that is being transmitted to the eardrum.

Some embodiments of the present invention provide significant improvement over conventional ear screening methods by taking into account of the retrograde waves. For example, some embodiments of the present invention derive a power measurement that reduces the effect of the retrograde waves on the power measurement, thereby making the measurement more accurate.

In some embodiments of the present invention, the incident wave pressure can be used for better hearing aid fitting.

With a more accurate measurement of the incident power to the ear drum, some embodiments of the present invention allow for a more reliable calibration of the audiometer.

With a more accurate measurement of the sound level delivered to the inner ear, some embodiments of the present invention allow for a more accurate result from the pure tone audiometry, distortion product otoacoustic emission measurements, transient otoacoustic emission measurements, and stimulus frequency otoacoustic emission measurements.

While many specific examples have been provided, the above description is intended to illustrate rather than limit the invention. Many variations of the invention will become apparent to those skilled in the art upon review of this specification. The scope of the invention should, therefore, be determined not with reference to the above description, but instead should be determined with reference to the appended claims along with their full scope of equivalents.

What is claimed is:

1. A method for characterizing an incident pressure wave in a hearing test, the method comprising:
    introducing a first sonic stimulus into an ear canal with a first sound source transducer positioned in an ear canal;
    measuring at least a frequency domain sound pressure signal ($P_m(f)$) in said ear canal with a receiving transducer in the ear canal;
    processing information, with a processor, associated with said sound pressure level;
    determining, with a processor, at least an acoustic reflectance ($R(f)$) including a real and imaginary part based on information associated with said sound pressure level;
    determining, with a processor, an incident wave pressure parameter ($P_+(f)$) in said ear canal according to:

$$P_+(f)=P_m(f)/(1+R(f));$$

determining, based on the incident wave pressure parameter ($P_+(f)$), with a processor, a voltage to apply to the first sound source transducer, to keep an incident wave pressure ($P_+(f)$) substantially constant with respect to frequency, wherein the voltage is a function of frequency and defined as to remove a standing wave field from measured sound pressure;
    wherein the first sonic stimulus is delivered to the ear canal by first source transducer situated near the opening of the ear canal.

2. A method for determining a hearing threshold, the method comprising:
    delivering a sonic stimulus associated with one or more frequencies and one or more volume levels to an ear canal with a source transducer positioned situated near the opening of the ear canal;
    measuring a sound signal ($P_m(f)$) with a receiving transducer positioned in the ear canal;
    determining, with one or more processors, at least an acoustic reflectance ($R(f)$), including a real and imaginary part, based on information associated with said sound pressure level;
    determining, with a one or more processors, an incident wave pressure parameter ($P_+(f)$) in said ear canal according to:

$$P_+(f)=P_m(f)/(1+R(f));\text{ and}$$

determining, with the one or more processors, a voltage to apply to the sound source transducer to keep an incident wave pressure parameter ($P_+(f)$) substantially constant with respect to frequency, wherein the voltage is a function of frequency;
    determining a threshold volume level, with a processor, for said sonic stimulus, wherein the threshold volume level is determined based on the constant incident wave pressure parameter ($P_+(f)$);
    measuring at least a sound pressure level of said ear canal at said threshold volume using said receiving transducer;
    processing information, with a one or more processors, associated with said measured sound pressure level;
    determining, with one or more processors, an acoustic reflectance based on at least information associated with said measured sound pressure level; and
    determining, with one or more processors, a threshold value for an incident wave pressure parameter in said ear canal based on at least information associated with said measured sound pressure level and said determined acoustic reflectance;
    wherein said threshold value for said incident wave pressure parameter representing said hearing threshold.

3. A system for calibrating hearing, the system comprising:
    a probe adapted to be placed near an opening of a ear canal, said probe comprises a source transducer for delivering a sonic stimulus associated with one or more frequencies and one or more intensity levels to an ear canal with the source transducer positioned situated near the opening of the ear canal;
    a signal generator connected to said source transducer, said signal generator being configured to send one or more first electronic signals to said source transducer for delivering said sound;
    a signal processor connected to said receiving transducer, said signal processor being configured to receive one or more second electronic signals from said receiving transducer and to determine at least a sound pressure level ($P_m(f)$) based on at least information associated with said one or more second electronic signals;
    a data processor connected to said signal processor, said data processor being configured to receive and process at least information associated with said determined sound pressure level ($P_m(f)$) and to determine an acoustic reflectance ($R(f)$);
    wherein said data processor is further configured to determine an incident wave pressure parameter ($P_+(f)$) in said ear canal according to:

$$P_+(f)=P_m(f)/(1+R(f))$$

wherein said data processor is further configured to determine, based on the incident wave pressure parameter ($P_+(f)$), a voltage to apply to the source transducer to keep an incident wave pressure parameter ($P_+(f)$) substantially constant with respect to frequency, wherein the voltage is a function of frequency.

4. The method of claim 1, wherein $P_m(f)$ is the frequency domain representation of the time-domain sound pressure signal $p_m(t)$ such that the frequency domain representation is selected from the group consisting of a Fourier transform and Laplace transform.

5. The method of claim 1, wherein $R(f)$ is the frequency domain representation of the time-domain acoustic reflectance $r(t)$ such that the frequency domain representation is selected from the group consisting of a Fourier transform and Laplace transform.

6. The method of claim 2, wherein $P_m(f)$ is the frequency domain representation of the time-domain sound pressure signal $p_m(t)$ such that the frequency domain representation is selected from the group consisting of a Fourier transform and Laplace transform.

7. The method of claim 2, wherein $R(f)$ is the frequency domain representation of the time-domain acoustic reflectance $r(t)$ such that the frequency domain representation is selected from the group consisting of a Fourier transform and Laplace transform.

8. The system of claim 3, wherein $P_m(f)$ is the frequency domain representation of the time-domain sound pressure signal $p_m(t)$ such that the frequency domain representation is selected from the group consisting of a Fourier transform and Laplace transform.

9. The system of claim 3, wherein $R(f)$ is the frequency domain representation of the time-domain acoustic reflectance r(t) such that the frequency domain representation is selected from the group consisting of a Fourier transform and Laplace transform.

* * * * *